(12) United States Patent
Padwa et al.

(10) Patent No.: US 9,462,981 B2
(45) Date of Patent: Oct. 11, 2016

(54) CONTROL PANEL FOR MEDICAL IMAGING SYSTEM

(71) Applicant: Arineta Ltd., Caesarea (IL)

(72) Inventors: Alexander Jonathan Padwa, Tel-Aviv (IL); Gilad Davidi, Tel-Aviv (IL)

(73) Assignee: Arineta Ltd., Caesarea (IL)

( * ) Notice: Subject to any disclaimer, the term of this patent is extended or adjusted under 35 U.S.C. 154(b) by 363 days.

(21) Appl. No.: 14/160,674

(22) Filed: Jan. 22, 2014

(65) Prior Publication Data

US 2015/0201891 A1    Jul. 23, 2015

(51) Int. Cl.
*A61B 5/05*   (2006.01)
*A61B 6/04*   (2006.01)
*A61B 6/03*   (2006.01)
*A61B 6/00*   (2006.01)

(52) U.S. Cl.
CPC ............ *A61B 6/0457* (2013.01); *A61B 6/032* (2013.01); *A61B 6/0407* (2013.01); *A61B 6/0492* (2013.01); *A61B 6/467* (2013.01)

(58) Field of Classification Search
CPC .. A61B 3/152; A61B 3/0025; A61B 5/0555; A61B 6/04; A61B 6/03; A61B 6/469
See application file for complete search history.

(56) References Cited

U.S. PATENT DOCUMENTS

| | | | |
|---|---|---|---|
| 6,490,476 B1 * | 12/2002 | Townsend | A61B 6/032 250/363.03 |
| 7,213,880 B2 | 5/2007 | Schmitz et al. | |
| 8,095,278 B2 | 1/2012 | Schaaf et al. | |
| 8,909,325 B2 * | 12/2014 | Kimchy | G01T 1/161 600/407 |
| 2002/0065461 A1 * | 5/2002 | Cosman | A61B 6/5247 600/426 |
| 2012/0220852 A1 | 8/2012 | Bentham et al. | |
| 2014/0155728 A1 * | 6/2014 | Lee | A61B 6/462 600/407 |

* cited by examiner

*Primary Examiner* — Joel Lamprecht

(57) ABSTRACT

A gantry control panel for positioning a patient with respect to a gantry includes at least one contour of at least a portion of a figure representing a patient to be positioned with respect to a gantry, and at least one control button positioned in association with the at least one contour or as part of the at least one contour. The at least one control button controls positioning of the patient with respect to the gantry.

20 Claims, 4 Drawing Sheets

CONTROL PANEL FOR MEDICAL IMAGING SYSTEM

FIELD AND BACKGROUND OF THE INVENTION

The present invention, in some embodiments thereof, relates to an ergonomic design for a control panel used for adjusting position of a person with respect to a machine and, more particularly, but not exclusively, to a control panel for adjusting position of a patient with respect to a gantry of a medical imaging system.

Medical imaging systems such as CT scanners, Positron Emission Tomography (PET) imaging systems and Nuclear Medicine (NM), e.g. Single-Photon Emission Computed Tomography (SPECT) imaging systems typically require positioning of a patient within a gantry. Typically, a patient's position is controlled with a motorized table on which the patient is supported. Typically, the table can be controlled to move in and out of the gantry and up and down, i.e. in a vertical direction. Some systems also allow for lateral adjustment i.e. left and right and tilting motion.

Prior to imaging, an operator typically helps a patient assume a required posture and aligns the patient with respect to the gantry using the movable table. The operator also typically uses light markers installed on the gantry for directing a beam on the patient from the gantry to obtain the proper patient alignment within field of view. Typically, the gantry includes a control panel that the operator can use to move the table and operate the markers. During the positioning procedure the operator is sometimes required to approach, engage and/or observe the patient from opposite sides of the gantry, e.g. left-right and back-front. Some imaging systems include more than one gantry control panel positioned on different sides of the gantry so that the operator can easily reach the control panels while engaging and/or observing the patient from the different positions.

Reference is now made to FIGS. 3A and 3B showing the LightSpeed VCT CT scanner offered by GE Healthcare as an exemplary system including a plurality of control panels for positioning a patient. The LightSpeed VCT CT scanner includes a gantry 10 with a plurality of control panels 12 on both the front face 11 and rear face 13 of the gantry. An operator uses control panel 12 for positioning table 7 within gantry 10. Typically, each of control panels 12 provide the same functionality and are identical or mirror images of each other, e.g. control panel 12 positioned on either side of gantry bore 8, e.g. on the left and right side of the gantry might be designed as mirror images of each other for aesthetic and/or usability purposes.

Reference is now made to FIGS. 4A and 4B showing the gantry control panel of the LightSpeed VCT offered by GE HealthCare. Typically, gantry control panel 12 includes a plurality of control buttons 121 for controlling movement of table 7, as well as a plurality of additional buttons 123 for operating the markers used for alignment and for operating the gantry. Typically, each of the buttons for moving the table has accompanying graphics to indicate a direction of movement of the table (FIG. 4B). For example buttons 5, 6 indicate moving the table toward and away from the gantry respectively while buttons 3, 4 indicate moving the table up or down respectively. In addition, the buttons are arrow shaped to indicate direction that the table will be moved. Additional buttons can indicate additional direction of movement, e.g. tilting of gantry 10 (buttons 15 and 16), or moving table 7 to a preset position (button 18). Typically, a same gantry control panel 12 (or mirror image) is positioned in a plurality of different positions on the gantry, e.g. left, right, front and rear. Control panel 12 will also typically include a display panel 19 displaying a timer for indicating an inter-scan delay period.

SUMMARY OF THE INVENTION

According to some embodiments of the present invention there is provided a control panel including buttons that are designed to be patient oriented instead of equipment oriented. An aspect of some embodiments of the present invention provides for a gantry control panel that is ergonomically designed to provide clear and/or intuitive indication regarding a direction of movement associated with buttons for moving a patient supported on a support structure and/or support table of gantry. According to some embodiments of the present invention, the indication is patient oriented. According to some embodiments of the present invention, the same control panel can be positioned in different orientations with respect to the gantry and still provide clear and intuitive indication regarding a direction of movement associated with buttons for moving a patient supported on a table of gantry. Optionally, the gantry control panel provides for intuitively moving a patient supported on the table in at least three different directions, e.g. up-down (direction of gravity), in-out of the gantry and left-right. Optionally, the gantry control panel provides for intuitively tilting the gantry or table in one or more directions.

An aspect of some embodiments of the present invention provides for a gantry control panel for positioning a patient with respect to a gantry, the control panel comprising: at least one contour of at least a portion of a figure representing a patient to be positioned with respect to a gantry; and at least one control button positioned in association with the at least one contour or as part of the at least one contour, wherein the at least one control button controls positioning of the patient with respect to the gantry.

Optionally, the contour comprises a graphic representation of a head of the figure and the at least one control button positioned in relation to the graphic representation of the head, wherein the graphic representation of the head and the at least one control button related thereto, together form at least a portion of the at least one contour.

Optionally, at least one of: the at least one control button, an indication light and a display screen is shaped as the graphic representation of the head of the figure.

Optionally, the at least one contour represents a torso of the patient.

Optionally, the at least one control button includes a control button for positioning the patient in a two-dimensional plane represented by the at least one contour.

Optionally, the at least one contour includes two contours of the figure, each of the two contours representing a view of the figure in a different plane.

Optionally, the at least one contour includes a first contour of a side view of the figure and a second contour of a front or rear view of the figure.

Optionally, the at least one control button includes one or more control buttons for moving the patient in and out of the gantry, wherein the control button for moving the patient in and out of the gantry is positioned in association with the contour in the side view.

Optionally, the at least one control button includes a control button for moving the patient in a vertical direction and wherein the control button for moving the patient in the vertical direction is positioned in association with the contour in the side view.

Optionally, the at least one control button includes a control button for shifting the patient in a lateral direction and wherein the control button for shifting the patient in a lateral direction is positioned in association with the second contour.

Optionally, the control button for shifting the patient in the lateral direction is positioned in association with a contour of the figure's left shoulder and operates to move the patient's left shoulder or arm shifts towards a wall of a bore of the gantry.

Optionally, the control button for shifting the patient in the lateral direction is positioned in association with a contour of the figure's right shoulder and operates to move the patient's right shoulder or arm shifts towards a wall of a bore of the gantry.

Optionally, the control panel includes a second control button other than the at least one control button for reversing a direction of movement associated with the at least one control button for moving a structure for supporting the patient.

Optionally, the at least one control button includes graphic markings to indicate a direction of movement.

Optionally, the control panel includes a representation of at least one of the gantry and a support table; and a third control button positioned in association with the representation of the at least one of the gantry and a support table.

Optionally, the representation of at least one of the gantry and the support table is positioned in association with the at least one contour of at least the portion of the figure representing the patient.

Optionally, the at least one control button includes a control button for operating markers that are installed on the gantry and operate to direct a beam on the patient and, wherein the control button for operating markers is positioned in association with the at least one contour of at least the portion of the figure representing the patient.

An aspect of some embodiments of the present invention provides for an imaging system with movable support structure for performing medical procedures on a patient and comprising: a gantry; a movable support structure that is operative to support the patient and move the patient with respect to the gantry; and at least one control panel as described herein above positioned on the gantry for controlling movement of the movable support structure.

Optionally, the control panel is positioned on both a front face and a rear face of the gantry.

Optionally, the support structure is a table or a chair.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DESCRIPTION OF SPECIFIC EMBODIMENTS OF THE INVENTION

Figure 1A:
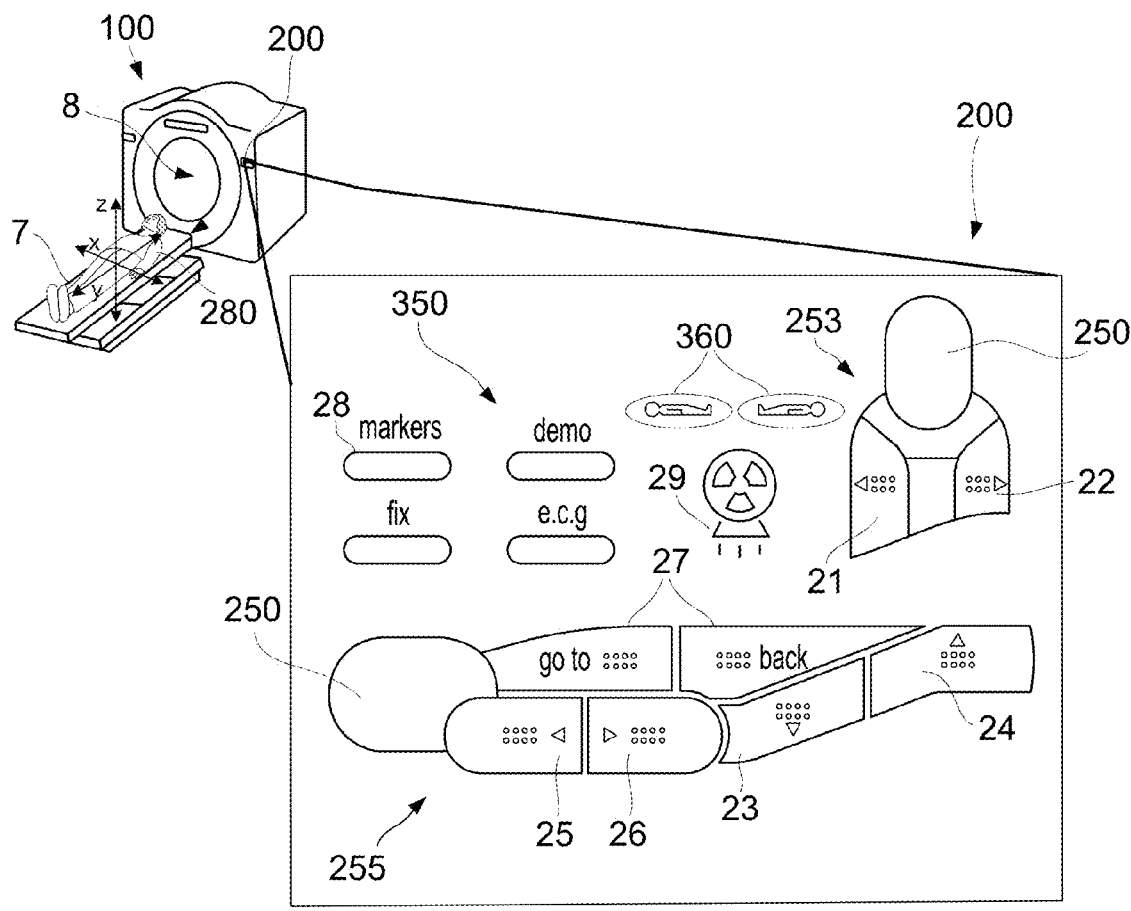
FIGS. 1A and 1B are schematic drawings of two exemplary gantry control panel in accordance with some embodiments of the present invention.

The present invention, in some embodiments thereof, relates to an ergonomic design for a control panel used for adjusting position of a person with respect to a machine and, more particularly, to a control panel for adjusting position of a patient with respect to a gantry of a medical imaging system.

The present inventors have found that operators of CT scanners and the like can easily be confused by the direction associated with the different control buttons of a gantry control panel. Although buttons for moving a support table up and down, e.g. along the vertical direction are typically clear regardless of where the control panel is positioned on the gantry, direction that are dependent on the orientation of the operator with respect to the machine often lead to confusion, e.g. left-right control and/or in-out control. This is especially the case when an operator uses a gantry control panel on both the front and rear face of the gantry. Additional confusion arises with gantry control panels that provide control in three dimensions. Typically, the direction of movement along the dimension that is perpendicular to the surface of the gantry control panel can be unclear. In addition lateral movement, e.g. parallel to the surface of the gantry control panel can be unclear. Further, additional confusion may arise when a gantry includes panels with different layouts (e.g. mirror layouts) so that buttons that provide a same function appear in different locations on different panels. The present inventors have found that ambiguity can be reduced by designing the control buttons to be patient oriented instead of equipment oriented.

According to some embodiments of the present invention, a gantry control panel includes a plurality of control buttons for moving the support table that are laid out in association with a graphic element representing a head of a person. In some exemplary embodiments, the control buttons are designed as a contour of body or part of a body positioned on the support table. Optionally, the buttons are shaped as part of a two dimensional contour of a body, e.g. shoulders or arms extending from the head. Optionally, the gantry and/or table are also represented in the layout of the buttons. The present inventors have found that by designing the buttons in relation to an element representing the head of the patient and integrating the buttons with a graphic representation of an extension of the body from the head, the designated direction that each button controls becomes clear and intuitive regardless of an operators orientation with respect to the gantry and/or position of the control panel on the gantry. For example, by positioning the lateral shift buttons, e.g. left-right on either side of the graphic element representing the head, the direction of movement of each of the lateral shift buttons becomes unambiguous from both the front and rear side of the gantry. In some exemplary embodiments, the head is graphically represented as an oval or rounded shaped element. Optionally, the graphic element representing the patient's head also serves as a control button and/or an indicating light. Optionally, the buttons are designed in relation to an element representing the head together with the torso and/or the head together with the body of the patient.

In some exemplary embodiments, more than one graphic representation of the head with associated control buttons representing different two dimensional planes of a patient is included in the gantry control panel, so that buttons controlling movement in each of the three dimensions can be clearly and intuitively laid out. Optionally, one graphic representation of the head with associated control buttons is laid out to represent a front view of the patient and another set of is laid out to represent a side view of the patient. Typically, the buttons that are laid out to represent the front view of the patient include buttons for shifting the table laterally, e.g. left or right and/or along the axis of the bore in the gantry while the buttons laid out to represent the side view include buttons for moving the table in the vertical direction and also for moving the table in and out of the gantry bore. Assuming that the patient is always positioned head first on the support table, this setup provides for clearly understanding the left-right direction and the in-out direction from any position on the gantry, e.g. from both front and rear face of the gantry. Optionally, the gantry control panel additionally includes a control button for reversing directions associated with one or more other control buttons in the case where the patient is positioned feet first on the support table. Optionally, reversal is controlled by software. Optionally, additional buttons that are not used for moving the table are also laid out along the contour of the figure extending from the head. Optionally, the control panel also includes one or more control buttons that are positioned to be unrelated to the contour of a patient.

Reference is now made to FIG. 1A showing a schematic drawing of an exemplary gantry control panel in accordance with some embodiments of the present invention. According to some embodiments of the present invention, a gantry control panel includes one or more contours, e.g. contours 253 and/or 255 of a figure and/or body including a head 250, the figure representing a patient 280 positioned on a movable table 7 of a gantry 100. Typically, each of contour 253 and contour 255 represents a figure of a person viewed from a different side and/or direction. In some exemplary embodiments, the contour of the figure extending from head 250 is formed and/or shaped with a group of control buttons, e.g. buttons 21-27 associated and/or positioned in relation to head 250, e.g. group 253 and/or group 255. In some exemplary embodiments, one or more buttons 21-27 include graphics, e.g. arrows and/or text to indicate a direction of movement of the patient and/or functionality associated with the control button. Optionally, the control buttons are shaped as arrows or are direction oriented and graphics markings are not used. Typically, at least some of the control buttons associated with the contours provide for positioning patient 280 with respect to gantry 100.

In some exemplary embodiments, a contour and/or a figure 255 of a side view of a person includes control buttons for moving patient 280 in a Y direction extending through gantry bore 8 and/or a Z direction extending vertically, e.g. in the direction of gravity. In some exemplary embodiments, contour 255 includes a control button 25 for moving patient 280 into gantry 100 and a control button 26 for moving patient 280 out of the gantry. The present inventors have found that movement into and out of gantry 100 can be clearly indicated by aligning buttons 25, 26 along a length of the contour representing a side view of the patient and by including arrows on the buttons that point toward and away from head 250. Optionally, control buttons 25 and 26 are positioned in association with a shoulder of contour 255. Optionally, one or more of the control buttons for positioning a patient, e.g. control buttons 25 and 26 is operated as a 3-way switch that provides for selecting between movement at a standard speed, e.g. when pressing a portion of the control button marked by a single arrow and a faster speed, e.g. when pressed on a portion marked by a double arrow. Alternatively, control buttons 25 and 26 can be replaced by a single button that is operated as a 3-way switch that provides for moving table 7 both in and out of gantry 100.

In some exemplary embodiments, a pair of control buttons 23, 24 for moving a patient up and down, e.g. in the Z direction is also included as part of contour 255. Optionally, the pair of control buttons 23, 24 is generally aligned perpendicular to a direction along which the contour representing a side view of the patient extends and includes arrows pointing up and down respectively to indicate raising and lowering of patient 280 supported on table 7. Optionally, a three way switch is used for raising and lowering.

Optionally, additional control buttons are included as part of contour 255 that control moving the patient, e.g. tilting gantry 100 and/or control other gantry functions. In some exemplary embodiments, a control button 28 for operating the markers of gantry 100 is included in contour 255. Optionally, one or more control buttons 27 for reaching pre-set and/or pre-stored positions is included in contour 255.

In some exemplary embodiments, control panel includes a contour 253 of a front view of a figure and includes one or more control buttons, e.g. control buttons 21-22 that are laid out to form and/or laid out in association with a contour of a front view of a body and/or patient with graphic representation of head 250. Contour 253 with control buttons can be in addition and/or in place of contour 255. The present inventors have found that functionality of the control buttons for moving a patient in three dimensions can be clearly and intuitively indicated when arranging the control buttons in association with both contour 253 in coronal plane and contour 255 in sagittal plane.

In some exemplary embodiments, contour 253 includes control buttons, e.g. control buttons 21 and 22 for moving patient 280 in an X direction extending laterally. Optionally, contour 253 includes control button 21 associated with a right shoulder of contour 253, e.g. positioned on the right shoulder of the contour that is operative to move patient 280 to the right and control button 22 associated with a left shoulder of contour 253, e.g. positioned on left shoulder of the contour is operative to move patient 280 to the left. Optionally, control buttons for moving a patient into and out of the gantry can be included in group 253 instead of in group 255.

In some exemplary, control panel 200 includes one or more additional control buttons that are not positioned in association with a contours 253 and 255. Optionally, control buttons 360 provides for reversing of the direction of movement associated with control buttons 21-28. Optionally, control buttons 360 provides for maintaining the patient oriented control of movements for different orientations of the patient, e.g. when the patient is positioned feet first or head first. The control button 360 that is selected is depressed to provide indication that allows an operator to know which orientation is activated. Optionally, control buttons 350 control operation of the gantry and/or control operation of one or more light markers installed on the gantry to obtain the proper alignment. Optionally, additional functions known in the art are controlled with control buttons 350. Typically, control buttons 350 do not include buttons for controlling movement of the patient. In some exemplary embodiments, control panel 200 additionally includes an indication light 29 and/or display screen. Optionally, graphic element representing a head 250 includes and/or functions as an indication light, speaker, display screen and/or a control button associated with operation of the gantry. Optionally, an indication light, speaker, display screen is used to provide feedback to the operator operating the gantry control panel.

Figure 1B:
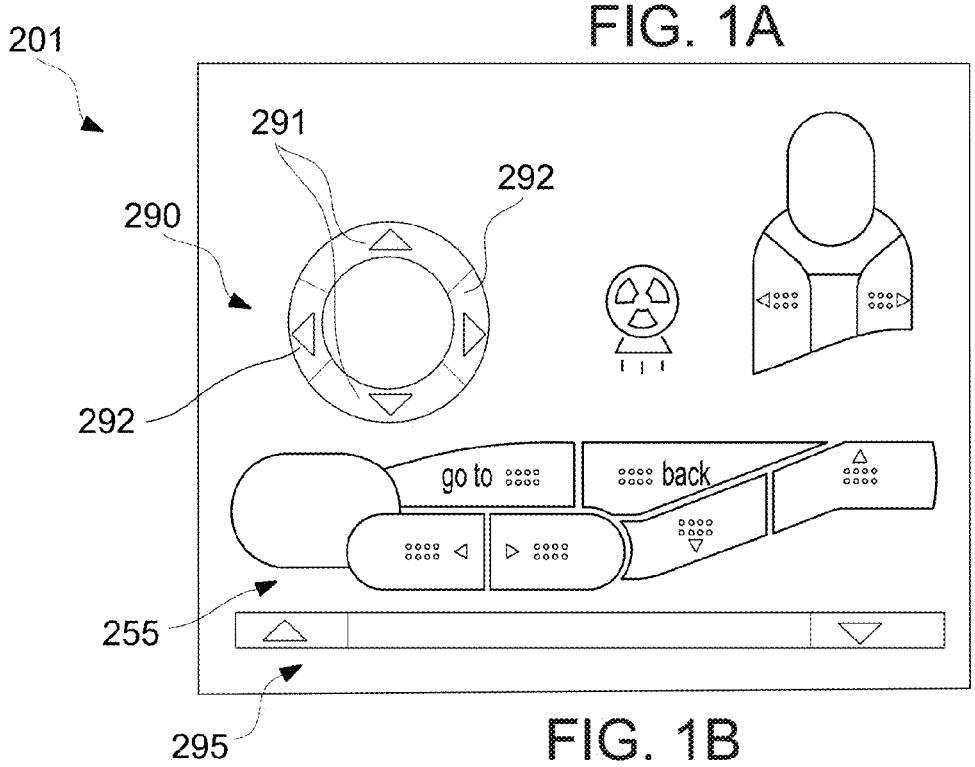

Reference is now made to FIG. 1B showing another schematic drawing of an exemplary gantry control panel in accordance with some embodiments of the present invention. According to some embodiments of the present invention, a gantry control panel 201 includes a contour 290 representing gantry 100. According to some embodiments of the present invention, contour 290 is associated with one or more control buttons 291 and/or 292 for controlling tilt of gantry 100. In some exemplary embodiments, control buttons 291 control tilting gantry 100 about the X axis and control buttons 292 control tilting about the Z axis. In some exemplary embodiments, gantry control panel 201 includes a contour 295 representing table 7. According to some embodiments of the present invention, contour 295 is positioned in relation to contour 255 of a figure representing the patient. Typically, contour 295 includes one or more control buttons for moving table 7.

Figure 2A:
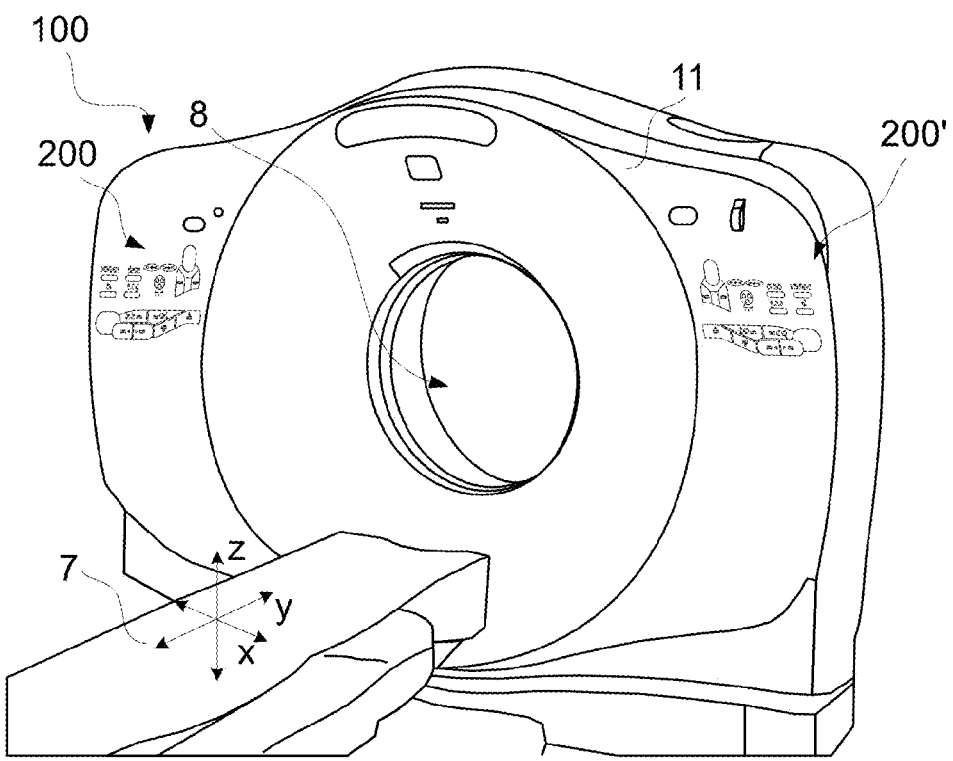
FIGS. 2A and 2B are schematic drawings of a front and rear face of a gantry, the gantry respectively including a plurality of gantry control panels in accordance with some embodiments of the present invention.
Figure 2B:
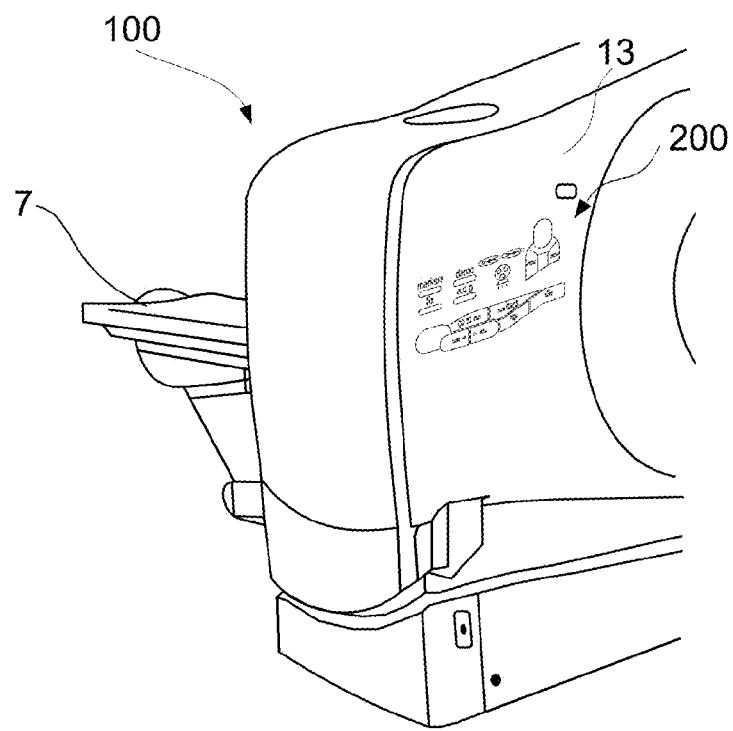
Figure 3A:
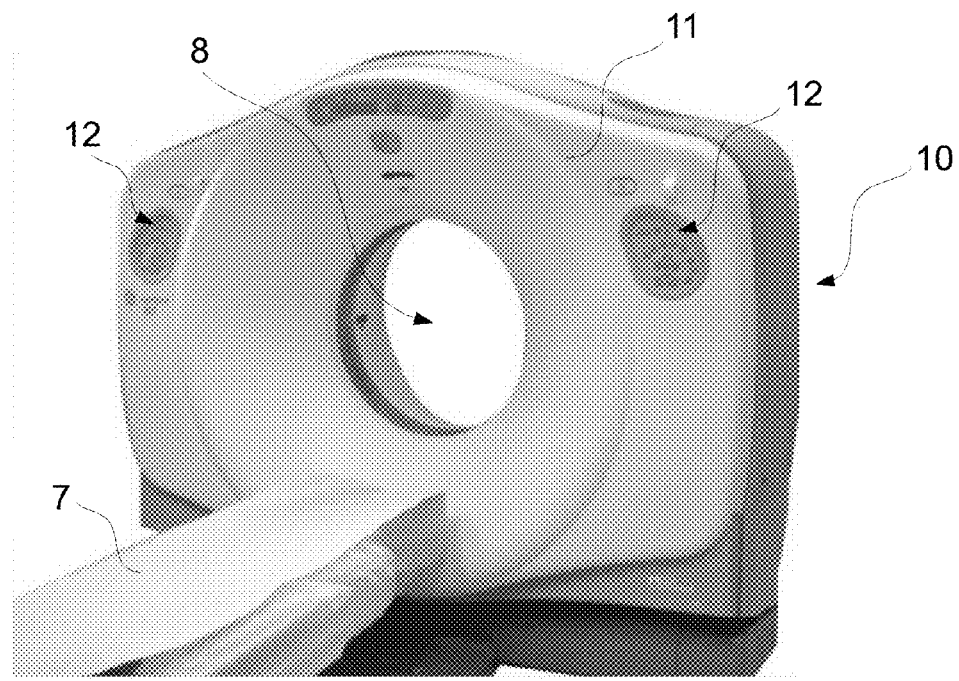
FIGS. 3A and 3B are images of the LightSpeed VCT CT scanner offered by GE Healthcare as an exemplary system according to the prior art including a plurality of control panels for positioning a patient.
Figure 3B:
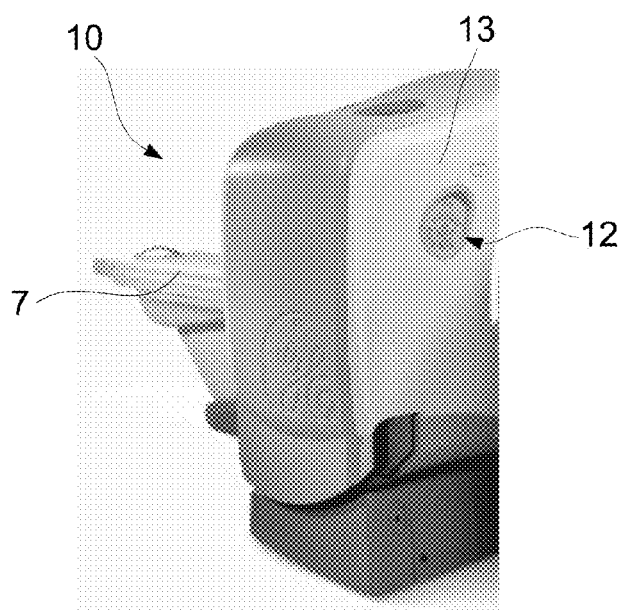
Figure 4A:
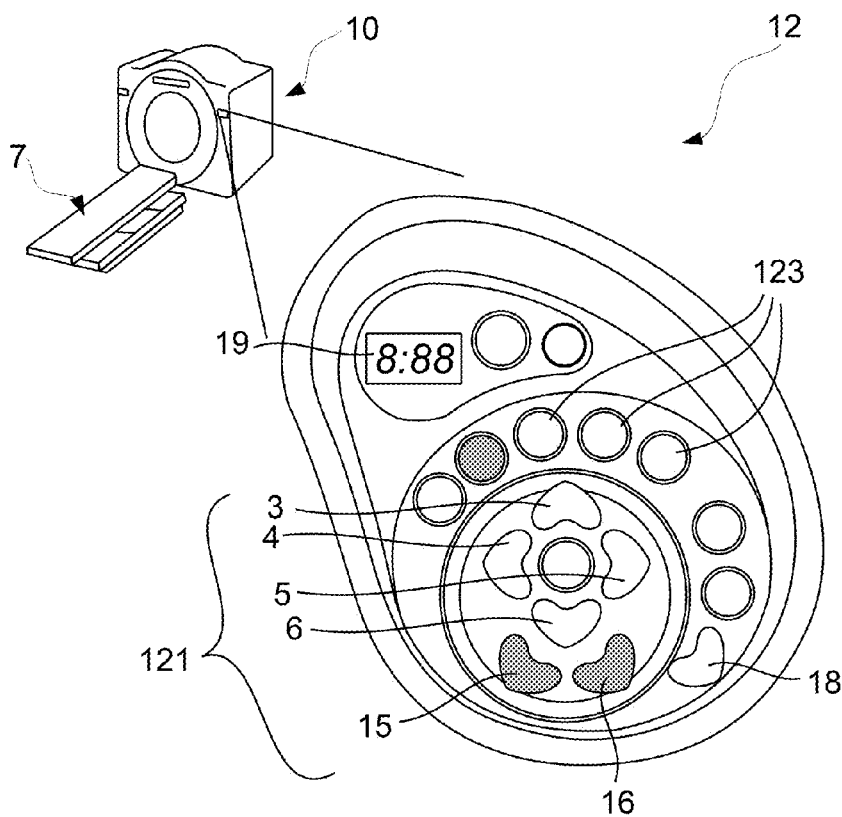
FIGS. 4A and 4B are a schematic drawing and image of the gantry control panel of the LightSpeed VCT according to the prior art as offered by GE HealthCare.
Figure 4B:
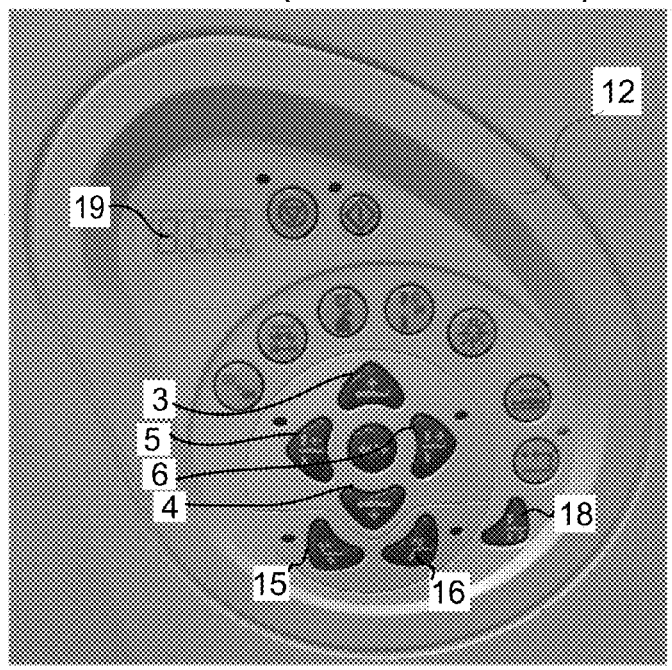

Reference is now made to FIGS. 2A and 2B showing schematic drawings of a front and rear face of a gantry, the gantry respectively including a plurality of gantry control panels in accordance with some embodiments of the present invention. According to some embodiments of the present invention, control panel 200 is positioned in a plurality of positions on a gantry 100. Optionally, control panel 200 is positioned on both a left and right side of gantry bore 8. Optionally, control panel 200 is positioned on a front face 11 and/or rear face 13 of gantry 100. In some exemplary embodiments, at least some of the control buttons in the control panels on either side of gantry bore 8 are laid out as mirror images of each other. The present inventors have found that since the control buttons in each of groups 253 and 255 are associated with an anatomy of the patient, it is clear what direction the patient will be moved when operating the control buttons regardless of the location of the operator with respect to the gantry. Alternatively, one or more of the control panels provide different functionality and include different control buttons than other control planes on gantry 100.

It is noted that although most of the embodiments of the present invention have been described in reference to buttons in a control panel, it would be understood by a person of ordinary skill in the art that the buttons can be replaced by switches, knobs, virtual buttons on a touch screen and the like. It is noted that although most of the embodiments of the present invention have been described in reference to buttons including graphic markings on the buttons, it would be understood by a person of ordinary skill in the art that graphic markings and be alternatively positioned below and/or above the buttons and/or that the buttons. It is also noted that although most of the embodiments of the present invention have been described in reference to a control panel that is mounted on a gantry, it would be understood by a person of ordinary skill in the art that the control panel can also be a standalone device, e.g. on a console hanging from the ceiling or a handheld remote control device.

It is noted that although most of the embodiments of the present invention have been described in reference to a gantry control panel including contours representing a front and side view of a patient, other controls representing other and/or additional views including also 3D views may be used.

It is noted that although most of the embodiments of the present invention have been described in reference to a gantry control panel including contours of a figure with a head, in some exemplary embodiments, the representation of the head may only be partially included or not included.

It is noted that although most of the embodiments of the present invention have been described in reference to a gantry control panel for a CT scanner, it would be understood by a person of ordinary skill in the art that a similar or same control panel can be applied for positioning a human subject supported on a motorized table, chair or the like relative to other radiological equipment, MRI, surgical equipment, and/or other systems including a gantry or the like, such as nuclear medicine imaging equipment.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination or as suitable in any other described embodiment of the invention. Certain features described in the context of various embodiments are not to be considered essential features of those embodiments, unless the embodiment is inoperative without those elements.

What is claimed is:

1. A gantry control panel for positioning a patient with respect to a gantry, the control panel comprising:
    a plurality of control buttons that are contoured and arranged with respect to one another to visually represent anatomical parts of a patient on a movable support structure of a medical imaging system;
    wherein the plurality of control buttons control positioning of the patient with respect to the gantry and wherein the contour and arrangement of the plurality of control buttons provides visual indication of a direction of movement of an anatomical part of the patient as actuated by each of the plurality of control buttons.

2. The control panel of claim 1 comprising graphic representation of a head of the patient, wherein the plurality of control buttons is positioned in relation to the graphic representation of the head.

3. The control panel of claim 2, wherein the graphic representation of the head is at least one of: a control button, an indication light and a display screen is shaped to visually represent the head.

4. The control panel of claim 1, wherein the plurality of control buttons visually represent a torso of the patient.

5. The control panel of claim 1, wherein the plurality of control buttons are contoured and arranged with respect to one another to visually represent anatomical parts of the patient in a two-dimensional plane.

6. The control panel of claim 1, wherein the plurality of control buttons are contoured and arranged with respect to one another to visually represent two separate views of the anatomical parts of patient, each view visually representing a different plane.

7. The control panel of claim 6, wherein the two separate views includes a first side view and a second front or rear view of the patient.

8. The control panel of claim 7, wherein the plurality of control buttons includes one or more control buttons for moving the patient in and out of the gantry, wherein the control button for moving the patient in and out of the gantry is included in the side view.

9. The control panel of claim 7, wherein the plurality of control buttons includes a control button for moving the patient in a vertical direction and wherein the control button for moving the patient in the vertical direction is included in the side view.

10. The control panel of claim 7, wherein the plurality of control buttons includes a control button for shifting the patient in a lateral direction and wherein the control button for shifting the patient in a lateral direction is included in the front or the rear view.

11. The control panel of claim 10, wherein the control button for shifting the patient in the lateral direction visually represents a left shoulder of the patient and operates to move the patient's left shoulder or arm towards a wall of a bore of the gantry.

12. The control panel of claim 10, wherein the control button for shifting the patient in the lateral direction is visually represents a right shoulder of the patient and operates to move the patient's right shoulder or arm shifts towards a wall of a bore of the gantry.

13. The control panel of claim 1, comprising a second control button other than the plurality of control buttons for reversing a direction of movement associated with the plurality of control buttons for moving a structure for supporting the patient.

14. The control panel of claim 1, wherein the plurality of control buttons includes graphic markings to indicate a direction of movement.

15. The control panel of claim 1, comprising:
a visual representation of at least one of the gantry and a support table; and
a third control button positioned in association with visual the representation of the at least one of the gantry and a support table.

16. The control panel of claim 15, wherein the visual representation of at least one of the gantry and the support table is positioned in association with the plurality of control buttons.

17. The control panel of claim 1, wherein the plurality of control buttons includes a control button for operating markers that are installed on the gantry and operate to direct a beam on the patient.

18. An imaging system with movable support structure for performing medical procedures on a patient and comprising:
a gantry;
a movable support structure that is operative to support the patient and move the patient with respect to the gantry; and
at least one control panel according to claim 1 positioned on the gantry for controlling movement of the movable support structure.

19. The imaging system with movable support structure of claim 18, wherein the control panel is positioned on both a front face and a rear face of the gantry.

20. The imaging system with movable support structure of claim 18, wherein the support structure is a table or a chair.

* * * * *